(12) United States Patent
Krzysik et al.

(10) Patent No.: US 7,268,104 B2
(45) Date of Patent: Sep. 11, 2007

(54) COLOR CHANGING LIQUID CLEANSING PRODUCTS

(75) Inventors: Duane G. Krzysik, Hudson, OH (US); Julie M. Utschig, Chicago, IL (US); Douglas Bryan Cole, Elkhart Lake, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 323 days.

(21) Appl. No.: 10/750,230

(22) Filed: Dec. 31, 2003

(65) Prior Publication Data

US 2005/0148490 A1    Jul. 7, 2005

(51) Int. Cl.
*C11D 1/14* (2006.01)
*C11D 1/90* (2006.01)
*C11D 3/04* (2006.01)
*C11D 3/06* (2006.01)

(52) U.S. Cl. ............... 510/124; 510/125; 510/127; 510/130; 510/137; 510/138; 510/417; 510/419; 424/70.21; 424/70.24

(58) Field of Classification Search ............... None
See application file for complete search history.

(56) References Cited

U.S. PATENT DOCUMENTS

| | | |
|---|---|---|
| 4,446,073 A | 5/1984 | Qualeatti et al. |
| 4,544,495 A | 10/1985 | Schmolka |
| 4,554,099 A | 11/1985 | Clarke |
| 4,642,198 A | 2/1987 | Humphreys et al. |
| 4,836,948 A | 6/1989 | Corring |
| 4,992,194 A | 2/1991 | Liberati et al. |
| 5,002,688 A | 3/1991 | Green et al. |
| 5,006,273 A | 4/1991 | Machin et al. |
| 5,017,296 A | 5/1991 | Nedonchelle |
| 5,019,289 A | 5/1991 | Gray et al. |
| 5,024,776 A | 6/1991 | Kreischer |
| 5,047,167 A | 9/1991 | Steyn et al. |
| 5,071,586 A | 12/1991 | Kaiserman et al. |
| 5,073,285 A | 12/1991 | Liberati et al. |
| 5,082,585 A | 1/1992 | Hessel et al. |
| 5,108,644 A | 4/1992 | Machin et al. |
| 5,147,576 A | 9/1992 | Montague et al. |
| 5,154,917 A | 10/1992 | Ibrahim et al. |
| 5,160,448 A | 11/1992 | Corring |
| 5,160,655 A | 11/1992 | Donker et al. |
| 5,205,957 A | 4/1993 | Van de Pas |
| 5,281,355 A | 1/1994 | Tsaur et al. |
| 5,281,356 A | 1/1994 | Tsaur et al. |
| 5,281,357 A | 1/1994 | Morgan et al. |
| 5,308,530 A | 5/1994 | Aronson et al. |
| 5,385,959 A | 1/1995 | Tsaur et al. |
| 5,397,493 A | 3/1995 | Potocki |
| 5,434,069 A | 7/1995 | Tsaur et al. |
| 5,441,660 A | 8/1995 | Tsaur et al. |
| 5,453,214 A | 9/1995 | van den Berg et al. |
| 5,464,552 A | 11/1995 | Peterson et al. |
| 5,476,519 A | 12/1995 | Haslop et al. |
| 5,529,724 A | 6/1996 | Falk |
| 5,547,918 A | 8/1996 | Newton et al. |
| 5,573,701 A | 11/1996 | Bulfari et al. |
| 5,597,508 A | 1/1997 | Schepers et al. |
| 5,633,223 A | 5/1997 | Vasudevan et al. |
| 5,672,580 A | 9/1997 | Donker et al. |
| 5,674,828 A | 10/1997 | Knowlton et al. |
| 5,712,239 A | 1/1998 | Knowlton et al. |
| 5,719,117 A | 2/1998 | Falk et al. |
| 5,723,434 A | 3/1998 | Falk et al. |
| 5,750,489 A | 5/1998 | Garcia et al. |
| 5,776,882 A | 7/1998 | Vasudevan |
| 5,776,883 A | 7/1998 | Vasudevan |
| 5,782,932 A | 7/1998 | van Dijk et al. |
| 5,807,810 A | 9/1998 | Blezard et al. |
| 5,846,927 A | 12/1998 | Vasudevan |
| 5,872,089 A | 2/1999 | Lo |
| 5,935,596 A | 8/1999 | Crotty et al. |
| 5,952,285 A | 9/1999 | Hawkins |
| 5,964,692 A | 10/1999 | Blezard et al. |
| 5,985,300 A | 11/1999 | Crotty et al. |
| 5,993,838 A | 11/1999 | Crotty et al. |
| 5,994,285 A | 11/1999 | Sachdev et al. |
| 6,010,994 A | 1/2000 | Choy et al. |
| 6,017,860 A | 1/2000 | Sajic et al. |
| 6,037,316 A | 3/2000 | Garner et al. |
| 6,046,150 A | 4/2000 | Choy et al. |
| 6,051,541 A | 4/2000 | Neuser et al. |
| 6,090,762 A | 7/2000 | Clapperton et al. |
| 6,106,857 A | 8/2000 | Crotty et al. |
| 6,166,095 A | 12/2000 | Bryan et al. |
| 6,177,396 B1 | 1/2001 | Clapperton et al. |
| 6,194,354 B1 | 2/2001 | Hatchman |
| 6,200,586 B1 | 3/2001 | Lambie et al. |
| 6,218,346 B1 | 4/2001 | Sajic et al. |
| 6,224,812 B1 | 5/2001 | Allan et al. |
| 6,241,976 B1 | 6/2001 | Esser et al. |
| 6,248,312 B1 | 6/2001 | Franklin et al. |
| 6,251,377 B1 | 6/2001 | Franklin |

(Continued)

FOREIGN PATENT DOCUMENTS

EP       0418049 A2    3/1991

(Continued)

OTHER PUBLICATIONS

International Search Report from PCT/US2004/025862 dated Jan. 27, 2005.

*Primary Examiner*—Gregory R. Del Cotto
(74) *Attorney, Agent, or Firm*—Senniger Powers

(57) ABSTRACT

Novel liquid cleansing products are disclosed. The cleansing products are comprised of a first colored structured liquid and a second colored structured liquid that when dispensed from a suitable dispenser, mix together to form a new colored cleansing product prior to, and during, use.

57 Claims, No Drawings

U.S. PATENT DOCUMENTS

| | | |
|---|---|---|
| 6,258,771 B1 | 7/2001 | Hsu et al. |
| 6,287,544 B1 | 9/2001 | Franklin et al. |
| 6,358,497 B2 | 3/2002 | Parry et al. |
| 6,361,766 B1 | 3/2002 | Franklin et al. |
| 6,362,156 B1 | 3/2002 | Hsu et al. |
| 6,369,018 B1 | 4/2002 | Hsu et al. |
| 6,387,358 B2 | 5/2002 | Chuah et al. |
| 6,391,291 B1 | 5/2002 | Clare et al. |
| 6,410,001 B1 | 6/2002 | Franklin et al. |
| 6,410,003 B1 | 6/2002 | Bhatia et al. |
| 6,426,060 B2 | 7/2002 | Franklin et al. |
| 6,426,326 B1 | 7/2002 | Mitra et al. |
| 6,455,056 B1 | 9/2002 | Franklin et al. |
| 6,458,344 B2 | 10/2002 | Franklin et al. |
| 6,462,013 B1 | 10/2002 | Cooke, Jr. et al. |
| 6,589,515 B2 | 7/2003 | Franklin et al. |
| 6,652,843 B2 | 11/2003 | Fairclough et al. |
| 2002/0128170 A1* | 9/2002 | DeClercq et al. ............ 510/521 |
| 2003/0139316 A1* | 7/2003 | Hsu et al. .................... 510/417 |
| 2003/0203830 A1* | 10/2003 | Zhu et al. .................... 510/407 |
| 2004/0248748 A1* | 12/2004 | Wei et al. .................... 510/130 |

FOREIGN PATENT DOCUMENTS

| | | |
|---|---|---|
| FR | 2648824 A1 | 12/1990 |
| FR | 2805162 A1 | 8/2001 |
| WO | WO 96/29047 A1 | 9/1996 |
| WO | WO 97/09957 A1 | 3/1997 |
| WO | WO 01/12150 A1 | 2/2001 |
| WO | WO 03/083033 A2 | 10/2003 |

* cited by examiner

COLOR CHANGING LIQUID CLEANSING PRODUCTS

BACKGROUND OF THE INVENTION

The present invention relates to liquid cleansing products for cleansing the skin and hair. More particularly, the present invention relates to structured cleansing compositions that change color upon dispensing from a container. The cleansing products are comprised of a first colored structured liquid and a second colored structured liquid that when dispensed from a suitable dispenser, mix together to form a new colored cleansing product prior to, and during, use.

An important hygiene habit for parents or caregivers to teach children is hand washing. Proper hand washing is an easy, quick, and effective way to prevent the transmission of bacteria, viruses, and other soils and contaminants at home, at school, and at daycare centers. Proper teaching of good hygiene habits to children can help prevent infection and illness during their early years, and can instill good sanitary habits throughout life.

The teaching of good hand washing habits to children not only includes how to effectively wash up, but also typically includes instructing a child when the appropriate times are for hand washing including, for example, after playing outside, after using the restroom, before eating, etc. As many parents and caregivers would recognize, teaching good hand washing habits to children is not an easy task. Many children are often preoccupied with other activities, making it difficult for a parent or caregiver to get the child's attention and direct them to a new task. Further, redirecting a child's attention may be even more difficult when the new task is considered by the child to be uninteresting.

In teaching good hand washing habits, parents and caregivers generally first introduce the child to the use of conventional soap and water. Although adults routinely use soap and water for hand washing, it can sometimes pose problems for a child. For example, one problem is that the child may use an inappropriate amount of soap. If the child uses too much soap, the excess soap may not be adequately rinsed away and may remain on the child's hands. Residual soap on the child's hands can be an irritant to the child's skin and eyes. Alternatively, if the child does not use a sufficient amount of soap, the hand washing may not be effective.

Another problem often encountered by parents and caregivers in teaching children good hand washing habits using conventional soap and water is that the child, if left unattended, may completely skip using the soap and simply rinse their hands with water. Failing to use soap during hand washing typically makes the washing ineffective.

Additionally, another problem encountered by parents and caregivers in teaching children to wash their hands with conventional soap and water is that it may be difficult to get the child to wash their hands for a time period sufficient to obtain effective cleansing. This problem may be compounded by the fact that it is often very difficult for children to judge how much time has elapsed during the hand washing exercise.

Based on the foregoing, it is clear that there is a need for a product that can effectively clean the hands and other skin in an easy to use, efficient manner such that children can easily use the product. Additionally, it would be beneficial if the product could attract and keep the interest of children; thereby, making it easier for a parent or caregiver to properly teach a child good hygiene habits.

SUMMARY OF THE INVENTION

The present invention is directed to structured cleansing compositions that change color upon dispensing from a container. The cleansing compositions are comprised of a first colored structured liquid and a second colored structured liquid. The first colored structured liquid and the second colored structured liquid are different colors. When the first colored structured liquid and the second colored structured liquid are dispensed from a suitable dispenser, they mix together to form a new colored cleansing product prior to, and during, use. Due to the structure and viscosity of the two colored structured liquids that comprise the structured cleansing compositions, the colors do not mix in the dispensing container prior to dispensing the product.

Therefore, the present invention is directed to a liquid color changing cleansing product comprising a first lamellar structured liquid and a second lamellar structured liquid. The first lamellar structured liquid comprises from about 10% (by weight) to about 80% (by weight) of a first surfactant, from about 0.1% (by weight) to about 10% (by weight) of a first electrolyte, and from about 0.001% (by weight) to about 10% (by weight) of a first coloring agent. The second lamellar structured liquid comprises from about 10% (by weight) to about 80% (by weight) of a second surfactant, from about 0.1% (by weight) to about 10% (by weight) of a second electrolyte, and from about 0.001% (by weight) to about 10% (by weight) of a second coloring agent. The first coloring agent and the second coloring agent are different coloring agents.

The present invention is further directed to a liquid color changing cleansing product comprising a first lamellar structured liquid and a second lamellar structured liquid. The first lamellar structured liquid comprises from about 10% (by weight) to about 80% (by weight) of a first surfactant, from about 0.1% (by weight) to about 10% (by weight) of a first electrolyte, from about 0.001% (by weight) to about 10% (by weight) of a first coloring agent, and no more than about 5% (by weight) of a first hydrophilic thickener. The second lamellar structured liquid comprises from about 10% (by weight) to about 80% (by weight) of a second surfactant, from about 0.1% (by weight) to about 10% (by weight) of a second electrolyte, from about 0.001% (by weight) to about 10% (by weight) of a second coloring agent, and no more than about 5% (by weight) of a second hydrophilic thickener. The first coloring agent and the second coloring agent are different coloring agents.

The present invention is further directed to a liquid color changing cleansing product comprising a first lamellar structured liquid and a second lamellar structured liquid. The first lamellar structured liquid comprises from about 10% (by weight) to about 80% (by weight) of a first surfactant selected from the group consisting of anionic surfactants, amphoteric surfactants, zwitterionic surfactants and mixtures thereof, from about 0.1% (by weight) to about 10% (by weight) of a first electrolyte, from about 0.001% (by weight) to about 10% (by weight) of a first coloring agent, no more than about 5% (by weight) of a first hydrophilic thickener, and no more than about 10% (by weight) of a first nonionic surfactant. The second lamellar structured liquid comprising from about 10% (by weight) to about 80% (by weight) of a second surfactant selected from the group consisting of anionic surfactants, amphoteric surfactants, zwitterionic surfactants, and mixtures thereof, from about 0.1% (by weight) to about 10% (by weight) of a second electrolyte, from about 0.001% (by weight) to about 10% (by weight) of a second coloring agent, no more than about 5% (by weight) of a second hydrophilic thickener, and no more than about 10% (by weight) of a second nonionic surfactant. The first coloring agent and the second coloring agent are different coloring agents.

The present invention is further directed to a liquid color changing cleansing product comprising a first substantially transparent liquid composition and a second colored liquid composition. The first substantially transparent liquid composition comprises from about 30% (by weight) to about 50% (by weight) of a first water soluble polysaccharide sugar, from about 5% (by weight) to about 30% (by weight) of a first surfactant, from about 1% (by weight) to about 10% (by weight) of a first water soluble salt, and the balance being an appropriate amount of water. The second colored liquid composition comprises from about 30% (by weight) to about 50% (by weight) of a second water soluble polysaccharide sugar, from about 5% (by weight) to about 30% (by weight) of a second surfactant, from about 1% (by weight) to about 10% (by weight) of a second water soluble salt, from about 0.001% (by weight) to about 10% (by weight) of a coloring agent, and the balance being an appropriate amount of water.

DETAILED DESCRIPTION OF THE PRESENTLY PREFERRED EMBODIMENTS

The present invention is generally directed to color changing cleansing products. The color changing cleansing products described herein include a first colored structured liquid and a second colored structured liquid wherein the first and second colored structured liquids are different colors. Upon the dispensing of the first and second colored structured liquids, they mix and a third, new color is formed in the hands of the user. Surprisingly, the first and second colored structured liquids do not mix in the single container from which they are dispensed prior to the dispensing of the liquids.

In accordance with the present invention, there are disclosed color changing cleansing products such as, for example, hand soaps, body soaps, body washes, shampoos, etc. These products change colors upon dispensing from a suitable dispenser, and/or upon the addition of water. These color change cleansing products generally comprise a first lamellar structured liquid and a second lamellar structured liquid. These first and second lamellar structured liquids are concentrated surfactant systems that have a lamellar structure typically in spherical or cubic form. In concentrated form, these systems have a lamellar structure but, upon the addition of water or the application of shear, or both, the lamellar structure is broken or diluted and the surfactants break into micellular form. As such, specific coloring agents as described herein can be introduced into the spherical or cubic lamellar structure and trapped within that structure until pumped from a dispenser and/or diluted with water. Once pumped and/or diluted with water, the lamellar structure breaks and the coloring agent is released. When a first lamellar structured liquid containing a first coloring agent and a second lamellar structured liquid containing a second coloring agent, wherein the first and second coloring agents are different coloring agents, are contained in the same dispenser, they will not mix or run together causing a color change until they are pumped from the dispenser causing shear to break the lamellar structure and/or diluted with water.

In one embodiment of the present invention, the first and second lamellar structured liquids containing the first and second coloring agents are introduced into a clear or translucent bottle-type dispenser simultaneously such that they do not mix together. The first and second lamellar structured liquids may be introduced at the same or different rates into the dispenser, and may be introduced in the same or different amounts. By using a clear or translucent bottle, the colors of the first and second lamellar structured liquids can be easily seen by a user of the product. Because the colors of the first and second lamellar structured liquids can be easily seen by a user, the user can also easily notice the color change that occurs when the first and second structured liquids are dispensed from the dispenser. One advantage of the products comprising the first lamellar structured liquid and second lamellar structured liquid described herein is that both of the structured liquids, which contain a coloring agent, may be introduced into a single dispenser without the need for a barrier between the two structured liquids; that is, because both liquids are structured liquids in lamellar phase with sufficient viscosity, these liquids will not come together during transport or storage and will only come together and provide the intended color change upon the addition of shear and/or water.

In one embodiment, the first and second lamellar structured liquids can be introduced into a pump-type or similar dispenser while the dispenser is being rotated slowly. This slow rotation of the dispenser during the filling of the first and second lamellar structured liquids results in a swirling of the first and second lamellar structured liquids; this leads to the first and second structured liquids, which are different colors, being swirled together in the dispenser. As such, upon dispensing, some of each of the first and second structured liquids are expressed and result in the color change of the formulation due to the mixing of the two formulations containing different colors and the shear applied during expression and/or the introduction of water during cleaning.

Alternatively, the first and second lamellar liquids can be introduced into a pump-type or similar dispenser from the bottom to the top utilizing a dip tube apparatus to produce a dispenser comprising the first colored lamellar structured liquid on one side of the dispenser and the second colored lamellar structured liquid on the other side of the dispenser. The pumping tube for dispensing the first and second lamellar structured liquids is then inserted into the dispenser down into the middle such that, upon pumping and activation of the dispensing unit, some of each of the first and second colored lamellar structured liquids are dispensed and mixed to produce the desired color change. It will be recognized by one skilled in the art based on the disclosure herein that the amount or degree of color change realized upon expression of the first and second lamellar structured liquids may not be to the same extent with each use as the dispenser may not express equivalent amounts of the first and second lamellar structured liquids each time it is used; that is, the degree of color change may vary from use to use. However, this variance in the amount of color change likely adds to the fun of using the cleansing product.

In an alternative embodiment, a double dip tube dispenser pump may be utilized to facilitate the mixing of the first and second colored lamellar structured liquids. In this embodiment, the first and second colored lamellar structured liquids are introduced into a dispenser side by side as described above and a double dip tube dispenser comprising two dip tubes is used to extract and mix the structured liquids. One of the double dip tubes is placed in the first colored lamellar structured liquid and the second dip tube is placed in the second colored lamellar structured liquid such that, upon pumping and/or activation, both liquids are drawn from the dispenser and brought together to cause a color change.

As noted above, the color change liquid cleansing products of the present invention comprise a first lamellar structured liquid and a second lamellar structured liquid, wherein the first and second lamellar structured liquids are different colors such that, upon the application of shear and/or water, they mix together and form a third, different color. Both the first and second lamellar structured liquids comprise a surfactant in an amount of from about 10% (by weight) to about 80% (by weight). As used herein, "by weight" refers to the total weight of the lamellar structured liquid. For example, if the first lamellar structured liquid has a total weight of 100 grams and comprises 80% (by weight) surfactant, the first lamellar structured liquid comprises 80 grams of surfactant. The surfactant is included in the liquids to provide a cleaning, lathering, and/or foaming action during the use of the product.

Suitable surfactants for use in the first and second lamellar structured liquids include anionic surfactants, amphoteric surfactants, zwitterionic surfactants, and combinations thereof. Suitable anionic surfactants include, for example, alkyl sulfates, alkyl ether sulfates, alkali metal or ammonia salts of alkyl sulfates, alkali metal or ammonia salts of alkyl ether sulfates, alkyl phosphates, alkyl glyceryl sulfonates, alkyl sulfosuccinates, alkyl taurates, acyl taurates, alkyl sarcosinates, acyl sarcosinates, sulfoacetates, alkyl phosphate esters, mono alkyl succinates, monoalkyl maleates, sulphoacetates, acyl isethionates, alkyl carboxylates, phosphate esters, and combinations thereof.

Suitable amphoteric surfactants include, for example, betaines, alkylamido betaines, sulfobetaines, N-alkyl betaines, sultaines, amphoacetates, diamophoacetates, imidazoline carboxylates, sarcosinates, acylamphoglycinates, such as cocamphocarboxyglycinates and acylamphopropionates, and combinations thereof.

Suitable zwitterionic surfactants include, for example, 4-[N,N-di(2-hydroxyethyl)-N-octadecylammonio]-butane-1-carboxylate, 5-[S-3-hydroxypropyl-S-hexadecylsulfonio]-3-hydroxypentane-1-sulfate, 3-[P,P-diethyl-P-3,6,9-trioxatetradexopcylphosphonio]-2-hydroxypropane-1-phosphate, 3-[N,N-dipropyl-N-3-dodecoxy-2-hydroxypropylammonio]-propane-1-phosphonate, 3-(N,N-dimethyl-N-hexadecylammonio)propane-1-sulfonate, 3-(N,N-dimethyl-N-hexadecylammonio)-2-hydroxypropane-1-sulfonate, 4-[N,N-di(2-hydroxyethyl)-N-(2-hydroxydodecyl)ammonio]-butane-1-carboxylate, 3-[S-ethyl-S-(3-dodecoxy-2-hydroxypropyl)sulfonio]-propane-1-phosphate, 3-[P,P-dimethyl-P-dodecylphosphonio]-propane-1-phosphonate, 5-[N,N-di(3-hydroxypropyl)-N-hexadecylammonio]-2-hydroxy-pentane-1-sulfate, and combinations thereof.

Along with the surfactant, both the first and second lamellar structured liquids additionally comprise an electrolyte in an amount of from about 0.1% (by weight) to about 5% (by weight). The electrolyte serves the function of a viscosity builder and/or a formulation stabilizer. Suitable electrolytes include, for example, sodium chloride, potassium chloride, ammonium chloride, sodium citrate, potassium citrate, sodium tripolyphosphate, potassium tripolyphosphate, and combinations thereof.

Additionally, both the first and second lamellar structured liquids comprise a coloring agent. In a preferred embodiment of the present invention, the first lamellar structured liquid and the second lamellar structured liquid comprise a different coloring agent; that is, the first and second structured liquids are colored differently such that upon combination, shear, and/or water, a color change occurs. Although typically less preferred, one of the first or second structured liquids may be colorless such that when combined with the other structured liquid which is colored, the color of the other structured liquid is paled by the addition of the colorless liquid.

Suitable coloring agents include, for example, dyes, color additives, and pigments or lakes. Suitable dyes include, for example, Blue 1, Blue 4, Brown 1, External Violet 2, External Violet 7, Green 3, Green 5, Green 8, Orange 4, Orange 5, Orange 10, Orange 11, Red 4, Red 6, Red 7, Red 17, Red 21, Red 22, Red 27, Red 28, Red 30, Red 31, Red 33, Red 34, Red 36, Red 40, Violet 2, Yellow 5, Yellow 6, Yellow 7, Yellow 8, Yellow 10, Yellow 11, Acid Red 195, Anthocyanins, Beetroot Red, Bromocresol Green, Bromothymol Blue, Capsanthin/Capsorubin, Curcumin, and Lactoflavin. Also, many dyes found suitable for use in the European Union and in Japan may be suitable for use as coloring agents in the present invention.

Suitable color additives include, for example, aluminum powder, annatto, bismuth citrate, bismuth oxychloride, bronze powder, caramel, carmine, beta carotene, chloraphyllin-copper complex, chromium hydroxide green, chromium oxide greens, copper powder, disodium EDTA-copper, ferric ammonium ferrocyanide, ferric ferrocyanide, guauazulene, guanine, henna, iron oxides, lead acetate, manganese violet, mica, pyrophylite, silver, titanium dioxide, ultramarines, zinc oxide, and combinations thereof.

Suitable pigments or lakes include, for example, Blue 1 Lake, External Yellow 7 Lake, Green 3 Lake, Orange 4 Lake, Orange 5 Lake, Orange 10 Lake, Red 4 Lake, Red 6 Lake, Red 7 Lake, Red 21 Lake, Red 22 Lake, Red 27 Lake, Red 28 Lake, Red 30 Lake, Red 31 Lake, Red 33 Lake, Red 36 Lake, Red 40 Lake, Yellow 5 Lake, Yellow 6 Lake, Yellow 7 Lake, Yellow 10 Lake, and combinations thereof.

As mentioned above, the first lamellar structured liquid and the second lamellar structured liquid are preferably colored differently. Further, the first and second lamellar structured liquids may also comprise the same or different surfactants or surfactant combinations, and/or the same or different electrolytes.

In another embodiment of the present invention, one or both of the first lamellar structured liquid and the second lamellar structured liquid may additionally comprise from about 1% (by weight) to about 5% (by weight) of a hydrophilic thickener. When included in the lamellar structured liquid, the hydrophilic thickener acts to thicken or increase the viscosity of the lamellar structured liquid. This may be advantageous in some embodiments where a thicker, or more viscous, product is desired. Suitable hydrophilic thickeners include, for example, xanthan gum, agar, alginates, carrageenan, furcellaran, guar, cationic guar, gum arabic, gum tragacanth, karaya gum, locust bean gum, dextran, starch, modified starches, gellan gum, carboxymethylcellulose, methyl hydroxypropylcellulose, hydroxypropylcellulose, hydroxyethylcellulose, propylene glycol alginate, hydroxypropyl guar, acrylates/$C_{10}$-$C_{30}$ alkyl acrylate crosspolymer, bentonite, laponite, hectorite, magnesium aluminum silicate, amylopectin, cellulose gum, carbomer, chitosan, modified chitosan, glyceryl methacrylate, polyquaterniums, PEG-150 pentaerythrityl tetrastearate, and combinations thereof.

In another embodiment of the present invention, one or both of the first lamellar structured liquid and the second lamellar structured liquid may additionally comprise from about 1% (by weight) to about 10% (by weight) of a nonionic surfactant. When included in the structured liquid, the nonionic surfactant may act to enhance the foaming properties of the resulting product during use; that is, the nonionic surfactant may improve the foaming properties of the product, and may provide a more compact, reduced bubble size or creamy foam. Suitable nonionic surfactants include, for example, mono and di alkanolamides such as, for example, cocamide MEA and cocamide DEA, amine oxides, alkyl polyglucosides, ethoxylated alcohols, ethoxylated carboxylic acids, ethoxylated amines, ethoxylated amides, ethoxylated alkylolamides, ethoxylated alkylphenols, ethoxylated glyceryl esters, ethoxylated sorbitan esters, ethoxylated phosphate esters, glycol stearate, glyceryl stearate, and combinations thereof. It will be recognized by one skilled in the art that many of the nonionic surfactants described herein may also act as thickening agents and may increase the viscosity of the liquids.

The first lamellar structured liquid and second lamellar structured liquid described herein both have a suitable viscosity such that, upon introduction into a suitable dispensing device, the liquids do not substantially flow together, yet are still capable of being easily pumped and dispensed from the dispensing unit. Each structured liquid has a viscosity of from about 10,000 cps to about 300,000 cps, desirably from about 25,000 cps to about 200,000 cps, and more desirably from about 50,000 cps to about 100,000 cps. The viscosities of the first lamellar structured liquid and second lamellar structured liquid may be the same, or may be different, depending upon the desired end product. In a preferred embodiment, the viscosities of the first lamellar structured liquid and the second lamellar structured liquid are within at least about 10%-20% of each other to minimize or eliminate bleed from one color into the other.

In another embodiment of the present invention, the color change liquid cleansing product may comprise a first substantially clear or transparent structured liquid in combination with a second colored structured liquid. The substantially clear or transparent liquid is comprised of from about 30% (by weight) to about 50% (by weight) of a first water soluble polysaccharide sugar, from about 5% (by weight) to about 30% (by weight) of a first anionic or nonionic surfactant, from about 1% (by weight) to about 10% (by weight) of a first water soluble salt, and from about 10% (by weight) to about 75% (by weight) water. The colored structured liquid is comprised of from about 30% (by weight) to about 50% (by weight) of a second water soluble polysaccharide sugar, from about 5% (by weight) to about 30% (by weight) of a second anionic or nonionic surfactant, from about 1% (by weight) to about 10% (by weight) of a second water soluble salt, from about 0.001% (by weight) to about 10% (by weight) of a coloring agent, and from about 10% (by weight) to about 75% (by weight) water.

Suitable water soluble polysaccharide sugars include, for example, fructose, sucrose and glucose. Suitable anionic and nonionic surfactants are described above.

The water soluble salt is used to lower the solubility of the surfactant in water. Suitable water soluble salts include sodium chloride, sodium citrate, sodium carbonate and the corresponding potassium and ammonium salts. Also, suitable coloring agents are described above.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. A liquid color changing cleansing product in a single container comprising a first lamellar structured liquid comprising from about 10% (by weight) to about 80% (by weight) of a first surfactant selected from the group consisting of anionic surfactants, amphoteric surfactants, zwitterionic surfactants, and combinations thereof, from about 0.1% (by weight) to about 10% (by weight) of a first electrolyte, and from about 0.001% (by weight) to about 10% (by weight) of a first coloring agent and a second lamellar structured liquid comprising from about 10% (by weight) to about 80% (by weight) of a second surfactant selected from the group consisting of anionic surfactants, amphoteric surfactants, zwitterionic surfactants, and combinations thereof, from about 0.1% (by weight) to about 10% (by weight) of a second electrolyte, and from about 0.001% (by weight) to about 10% (by weight) of a second coloring agent, wherein the first coloring agent and the second coloring agent are different coloring agents, and wherein the first lamellar structured liquid and the second lamellar structured liquid each have a viscosity of from about 25,000 cps to about 200,000 cps.

2. The liquid color changing cleansing product as set forth in claim 1 wherein the first lamellar structured liquid and the second lamellar structured liquid each have a viscosity from about 50,000 cps to about 100,000 cps.

3. The liquid color changing cleansing product as set forth in claim 1 wherein the anionic surfactants are selected from the group consisting of alkyl sulfates, alkyl ether sulfates, alkali metal or ammonia salts of alkyl sulfates, alkali metal or ammonia salts of alkyl ether sulfates, alkyl phosphates, alkyl glyceryl sulfonates, alkyl sulfosuccinates, alkyl taurates, acyl taurates, alkyl sarcosinates, acyl sarcosinates, sulfoacetates, alkyl phosphate esters, mono alkyl succinates, monoalkyl maleates, sulphoacetates, acyl isethionates, alkyl carboxylates, phosphate esters, and combinations thereof.

4. The liquid color changing cleansing product as set forth in claim 1 wherein the amphoteric surfactants are selected from the group consisting of betaines, alkylamido betaines, sulfobetaines, N-alkyl betaines, sultaines, amphoacetates, diamophoacetates, imidazoline carboxylates, sarcosinates, acylamphoglycinates, and combinations thereof.

5. The liquid color changing cleansing product as set forth in claim 4 wherein the acylamphoglycinates are selected from the group consisting of cocamphocarboxyglycinates and acylamphopropionates.

6. The liquid color changing cleansing product as set forth in claim 1 wherein the zwitterionic surfactants are selected from the group consisting of 4-[N,N-di(2-hydroxyethyl)-N-octadecylammonio]-butane-1-carboxylate, 5-[S-3-hydroxypropyl-S-hexadecylsulfonio]-3-hydroxypentane-1-sulfate, 3-[P,P-diethyl-P-3,6,9-trioxatetradexopcylphosphonio]-2-hydroxypropane-1-phosphate, 3-[N,N-dipropyl-N-3-dodecoxy-2-hydroxypropylammonio]-propane-1-phosphonate, 3-(N,N-dimethyl-N-hexadecylammonio)propane-1-sulfonate, 3-(N,N-dimethyl-N-hexadecylammonio)-2-hydroxypropane-1-sulfonate, 4-[N,N-di(2-hydroxyethyl)-N-(2-hydroxydodecyl)ammonio]-butane-1-carboxylate, 3-[S-ethyl- S-(3-dodecoxy-2-hydroxypropyl)sulfonio]-propane-1-phosphate, 3-[P,P -dimethyl-P-dodecylphosphonio]-propane-1-phosphonate, 5-[N,N -di(3-hydroxypropyl)-N-hexadecylammonio]-2-hydroxy-pentane-1-sulfate, and combinations thereof.

7. The liquid color changing cleansing product as set forth in claim 1 wherein the first electrolyte and second electrolyte are selected from the group consisting of sodium chloride, potassium chloride, ammonium chloride, sodium citrate, potassium citrate, sodium tripolyphosphate, and potassium tripolyphophate.

8. The liquid color changing cleansing product as set forth in claim 1 wherein the first coloring agent and second coloring agent are dyes.

9. The liquid color changing cleansing product as set forth in claim 8 wherein the dyes are selected from the group consisting of Blue 1, Blue 4, Brown 1, External Violet 2, External Violet 7, Green 3, Green 5, Green 8, Orange 4, Orange 5, Orange 10, Orange 11, Red 4, Red 6, Red 7, Red 17, Red 21, Red 22, Red 27, Red 28, Red 30, Red 31, Red 33, Red 34, Red 36, Red 40, Violet 2, Yellow 5, Yellow 6, Yellow 7, Yellow 8, Yellow 10, Yellow 11, Acid Red 195, Anthocyanins, Beetroot Red, Bromocresol Green, Bromothymol Blue, Capsanthin/Capsorubin, Curcumin, and Lactoflavin.

10. The liquid color changing cleansing product as set forth in claim 1 wherein the first coloring agent and second coloring agent are color additives.

11. The liquid color changing cleansing product as set forth in claim 10 wherein the color additives are selected from the group consisting of aluminum powder, annatto, bismuth citrate, bismuth oxychloride, bronze powder, caramel, carmine, beta carotene, chloraphyllin-copper complex, chromium hydroxide green, chromium oxide greens, copper powder, disodium EDTA-copper, ferric ammonium ferrocyanide, ferric ferrocyanide, guauazulene, guanine, henna, iron oxides, lead acetate, maganese violet, mica, pyrophylite, silver, titanium dioxide, ultramarines, and zinc oxide.

12. The liquid color changing cleansing product as set forth in claim 1 wherein the first coloring agent and second coloring agent are pigments or lakes.

13. The liquid color changing cleansing product as set forth in claim 12 wherein the pigments or lakes are selected from the group consisting of Blue 1 Lake, External Yellow 7 Lake, Green 3 Lake, Orange 4 Lake, Orange 5 Lake, Orange 10 Lake, Red 4 Lake, Red 6 Lake, Red 7 Lake, Red 21 Lake, Red 22 Lake, Red 27 Lake, Red 28 Lake, Red 30 Lake, Red 31 Lake, Red 33 Lake, Red 36 Lake, Red 40 Lake, Yellow 5 Lake, Yellow 6 Lake, Yellow 7 Lake, and Yellow 10 Lake.

14. A liquid color changing cleansing product in a single container comprising a first lamellar structured liquid comprising from about 10% (by weight) to about 80% (by weight) of a first surfactant selected from the group consisting of anionic surfactants, amphoteric surfactants, zwitterionic surfactants, and combinations thereof, from about 0.1% (by weight) to about 10% (by weight) of a first electrolyte, from about 0.001% (by weight) to about 10% (by weight) of a first coloring agent, and no more than about 5% (by weight) of a first hydrophilic thickener, and a second lamellar structured liquid comprising from about 10% (by weight) to about 80% (by weight) of a second surfactant selected from the group consisting of anionic surfactants, amphoteric surfactants, zwitterionic surfactants, and combinations thereof, from about 0.1% (by weight) to about 10% (by weight) of a second electrolyte, from about 0.001% (by weight) to about 10% (by weight) of a second coloring agent, and no more than about 5% (by weight) of a second hydrophilic thickener, wherein the first coloring agent and the second coloring agent are different coloring agents, and wherein the first lamellar structured liquid and the second lamellar structured liquid each have a viscosity of from about 25,000 cps to about 200,000 cps.

15. The liquid color changing cleansing product as set forth in claim 14 wherein the first lamellar structured liquid and the second lamellar structured liquid each have a viscosity from about 50,000 cps to about 100,000 cps.

16. The liquid color changing cleansing product as set forth in claim 14 wherein the anionic surfactants are selected from the group consisting of alkyl sulfates, alkyl ether sulfates, alkali metal or ammonia salts of alkyl sulfates, alkali metal or ammonia salts of alkyl ether sulfates, alkyl phosphates, alkyl glyceryl sulfonates, alkyl sulfosuccinates, alkyl taurates, acyl taurates, alkyl sarcosinates, acyl sarcosinates, sulfoacetates, alkyl phosphate esters, mono alkyl succinates, monoalkyl maleates, sulphoacetates, acyl isethionates, alkyl carboxylates, phosphate esters, and combinations thereof.

17. The liquid color changing cleansing product as set forth in claim 14 wherein the amphoteric surfactants are selected from the group consisting of betaines, alkylamido betaines, sulfobetaines, N-alkyl betaines, sultaines, amphoacetates, diamophoacetates, imidazoline carboxylates, sarcosinates, acylamphoglycinates, and combinations thereof.

18. The liquid color changing cleansing product as set forth in claim 17 wherein the acylamphoglycinates are selected from the group consisting of cocamphocarboxyglycinates and acylamphopropionates.

19. The liquid color changing cleansing product as set forth in claim 14 wherein the zwitterionic surfactants are selected from the group consisting of 4-[N,N-di(2-hydroxyethyl)-N-octadecylammonio]-butane-1-carboxylate, 5-[S-3-hydroxypropyl-S-hexadecylsulfonio]-3-hydroxypentane-1-sulfate, 3-[P,P-diethyl-P-3,6,9-trioxatetradexopcylphosphonio]-2-hydroxypropane-1-phosphate, 3-[N,N-dipropyl-N-3-dodecoxy-2-hydroxypropylammonio]-propane-1-phosphonate, 3-(N,N-dimethyl-N-hexadecylammonio)propane-1-sulfonate, 3-(N,N-dimethyl-N-hexadecylammonio)-2-hydroxypropane-1-sulfonate, 4-[N,N-di(2-hydroxyethyl)-N-(2-hydroxydodecyl)ammonio]-butane-1-carboxylate, 3-[S-ethyl-S-(3-dodecoxy-2-hydroxypropyl)sulfonio]-propane-1-phosphate, 3-[P,P -dimethyl-P-dodecylphosphonio]-propane-1-phosphonate, 5-[N,N -di(3-hydroxypropyl)-N-hexadecylammonio]-2-hydroxy-pentane-1-sulfate, and combinations thereof.

20. The liquid color changing cleansing product as set forth in claim 14 wherein the first electrolyte and second electrolyte are selected from the group consisting of sodium chloride, potassium chloride, ammonium chloride, sodium citrate, potassium citrate, sodium tripolyphosphate, and potassium tripolyphophate.

21. The liquid color changing cleansing product as set forth in claim 14 wherein the first coloring agent and second coloring agent are dyes.

22. The liquid color changing cleansing product as set forth in claim 21 wherein the dyes are selected from the group consisting of Blue 1, Blue 4, Brown 1, External Violet 2, External Violet 7, Green 3, Green 5, Green 8, Orange 4, Orange 5, Orange 10, Orange 11, Red 4, Red 6, Red 7, Red 17, Red 21, Red 22, Red 27, Red 28, Red 30, Red 31, Red 33, Red 34, Red 36, Red 40, Violet 2, Yellow 5, Yellow 6, Yellow 7, Yellow 8, Yellow 10, Yellow 11, Acid Red 195, Anthocyanins, Beetroot Red, Bromocresol Green, Bromothymol Blue, Capsanthin/Capsorubin, Curcumin, and Lactoflavin.

23. The liquid color changing cleansing product as set forth in claim 14 wherein the first coloring agent and second coloring agent are color additives.

24. The liquid color changing cleansing product as set forth in claim 23 wherein the color additives are selected from the group consisting of aluminum powder, annatto, bismuth citrate, bismuth oxychloride, bronze powder, caramel, carmine, beta carotene, chloraphyllin-copper complex, chromium hydroxide green, chromium oxide greens, copper powder, disodium EDTA-copper, ferric ammonium ferrocyanide, ferric ferrocyanide, guauazulene, guanine, henna, iron oxides, lead acetate, maganese violet, mica, pyrophylite, silver, titanium dioxide, ultramarines, and zinc oxide.

25. The liquid color changing cleansing product as set forth in claim 14 wherein the first coloring agent and second coloring agent are pigments or lakes.

26. The liquid color changing cleansing product as set forth in claim 25 wherein the pigments or lakes are selected from the group consisting of Blue 1 Lake, External Yellow 7 Lake, Green 3 Lake, Orange 4 Lake, Orange 5 Lake, Orange 10 Lake, Red 4 Lake, Red 6 Lake, Red 7 Lake, Red 21 Lake, Red 22 Lake, Red 27 Lake, Red 28 Lake, Red 30 Lake, Red 31 Lake, Red 33 Lake, Red 36 Lake, Red 40 Lake, Yellow 5 Lake, Yellow 6 Lake, Yellow 7 Lake, and Yellow 10 Lake.

27. The liquid color changing cleansing product as set forth in claim 14 wherein the first hydrophilic thickener and second hydrophilic thickener are selected from the group consisting of xanthan gum, agar, alginates, carrageenan, furcellaran, guar, cationic guar, gum arabic, gum tragacanth, karaya gum, locust bean gum, dextran, starch, modified starches, gellan gum, carboxymethylcellulose, methyl hydroxypropylcellulose, hydroxypropylcellulose, hydroyethylcellulose, propylene glycol alginate, hydroxypropyl guar, acrylates/$C_{10}$-$C_{30}$ alkyl acrylate crosspolymer, bentonite, laponite, hectorite, magnesium aluminum silicate, amylopectin, cellulose gum, carbomer, chitosan, modified chitosan, glyceryl methacrylate, polyquaterniums, PEG-150 pentaerythrityl tetrastearate, and combinations thereof.

28. A liquid color changing cleansing product in a single container comprising a first lamellar structured liquid comprising from about 10% (by weight) to about 80% (by weight) of a first surfactant selected from the group consisting of anionic surfactants, amphoteric surfactants, zwitterionic surfactant and mixtures thereof, from about 0.1% (by weight) to about 10% (by weight) of a first electrolyte, from about 0.001% (by weight) to about 10% (by weight) of a first coloring agent, no more than about 5% (by weight) of a first hydrophilic thickener, and no more than about 10% (by weight) of a first nonionic surfactant, and a second lamellar structured liquid comprising from about 10% (by weight) to about 80% (by weight) of a second surfactant selected from the group consisting of anionic surfactants, amphoteric surfactants, zwitterionic surfactants, and mixtures thereof, from about 0.1% (by weight) to about 10% (by weight) of a second electrolyte, from about 0.001% (by weight) to about 10% (by weight) of a second coloring agent, no more than about 5% (by weight) of a second hydrophilic thickener, and no more than about 10% (by weight) of a second nonionic surfactant, wherein the first coloring agent and the second coloring agent are different coloring agents, and wherein the first lamellar structured liquid and the second lamellar structured liquid each have a viscosity of from about 25,000 cps to about 200,000 cps.

29. The liquid color changing cleansing product as set forth in claim 28 wherein the first lamellar structured liquid and the second lamellar structured liquid each have a viscosity from about 50,000 cps to about 100,000 cps.

30. The liquid color changing cleansing product as set forth in claim 28 wherein the anionic surfactants are selected from the group consisting of alkyl sulfates, alkyl ether sulfates, alkali metal or ammonia salts of alkyl sulfates, alkali metal or ammonia salts of alkyl ether sulfates, alkyl phosphates, alkyl glyceryl sulfonates, alkyl sulfosuccinates, alkyl taurates, acyl taurates, alkyl sarcosinates, acyl sarcosinates, sulfoacetates, alkyl phosphate esters, mono alkyl succinates, monoalkyl maleates, sulphoacetates, acyl isethionates, alkyl carboxylates, phosphate esters, and combinations thereof.

31. The liquid color changing cleansing product as set forth in claim 28 wherein the amphoteric surfactants are selected from the group consisting of betaines, alkylamido betaines, sulfobetaines, N-alkyl betaines, sultaines, amphoacetates, diamophoacetates, imidazoline carboxylates, sarcosinates, acylamphoglycinates, and combinations thereof.

32. The liquid color changing cleansing product as set forth in claim 31 wherein the acylamphoglycinates are selected from the group consisting of cocamphocarboxyglycinates and acylamphopropionates.

33. The liquid color changing cleansing product as set forth in claim 28 wherein the zwitterionic surfactants are selected from the group consisting of 4-[N,N-di(2-hydroxyethyl)-N-octadecylammonio]-butane-1-carboxylate, 5-[S-3-hydroxypropyl-S-hexadecylsulfonio]-3-hydroxypentane-1-sulfate, 3-[P,P-diethyl-P-3,6,9-trioxatetradexopcylphosphonio]-2-hydroxypropane-1-phosphate, 3-[N,N-dipropyl-N-3-dodecoxy-2-hydroxypropylammonio]-propane-1-phosphonate, 3-(N,N-dimethyl-N-hexadecylammonio)propane-1-sulfonate, 3-(N,N-dimethyl-N-hexadecylammonio)-2-hydroxypropane-1-sulfonate, 4-[N,N-di(2-hydroxyethyl)-N-(2-hydroxydodecyl)ammonio]-butane-1-carboxylate, 3-[S-ethyl-S-(3-dodecoxy-2-hydroxypropyl)sulfonio]-propane-1-phosphate, 3-[P,P-dimethyl-P-dodecylphosphonio]-propane-1-phosphonate, 5-[N,N-di(3-hydroxypropyl)-N-hexadecylammonio]-2-hydroxy-pentane-1-sulfate, and combinations thereof.

34. The liquid color changing cleansing product as set forth in claim 28 wherein the first electrolyte and second electrolyte are selected from the group consisting of sodium chloride, potassium chloride, ammonium chloride, sodium citrate, potassium citrate, sodium tripolyphosphate, and potassium tripolyphophate.

35. The liquid color changing cleansing product as set forth in claim 28 wherein the first coloring agent and second coloring agent are dyes.

36. The liquid color changing cleansing product as set forth in claim 35 wherein the dyes are selected from the group consisting of Blue 1, Blue 4, Brown 1, External Violet 2, External Violet 7, Green 3, Green 5, Green 8, Orange 4, Orange 5, Orange 10, Orange 11, Red 4, Red 6, Red 7, Red 17, Red 21, Red 22, Red 27, Red 28, Red 30, Red 31, Red 33, Red 34, Red 36, Red 40, Violet 2, Yellow 5, Yellow 6, Yellow 7, Yellow 8, Yellow 10, Yellow 11, Acid Red 195, Anthocyanins, Beetroot Red, Bromocresol Green, Bromothymol Blue, Capsanthin/Capsorubin, Curcumin, and Lactoflavin.

37. The liquid color changing cleansing product as set forth in claim 28 wherein the first coloring agent and second coloring agent are color additives.

38. The liquid color changing cleansing product as set forth in claim 37 wherein the color additives are selected from the group consisting of aluminum powder, annatto, bismuth citrate, bismuth oxychloride, bronze powder, caramel, carmine, beta carotene, chloraphyllin-copper complex, chromium hydroxide green, chromium oxide greens, copper powder, disodium EDTA-copper, ferric ammonium ferrocyanide, ferric ferrocyanide, guauazulene, guanine, henna, iron oxides, lead acetate, maganese violet, mica, pyrophylite, silver, titanium dioxide, ultramarines, and zinc oxide.

39. The liquid color changing cleansing product as set forth in claim 28 wherein the first coloring agent and second coloring agent are pigments or lakes.

40. The liquid color changing cleansing product as set forth in claim 39 wherein the pigments or lakes are selected from the group consisting of Blue 1 Lake, External Yellow 7 Lake, Green 3 Lake, Orange 4 Lake, Orange 5 Lake, Orange 10 Lake, Red 4 Lake, Red 6 Lake, Red 7 Lake, Red 21 Lake, Red 22 Lake, Red 27 Lake, Red 28 Lake, Red 30 Lake, Red 31 Lake, Red 33 Lake, Red 36 Lake, Red 40 Lake, Yellow 5 Lake, Yellow 6 Lake, Yellow 7 Lake, and Yellow 10 Lake.

41. The liquid color changing cleansing product as set forth in claim 28 wherein the first hydrophilic thickener and second hydrophilic thickener are selected from the group consisting of xanthan gum, agar, alginates, carrageenan, furcellaran, guar, cationic guar, gum arabic, gum tragacanth, karaya gum, locust bean gum, dextran, starch, modified starches, gellan gum, carboxymethylcellulose, methyl hydroxypropylcellulose, hydroxypropylcellulose, hydroyethylcellulose, propylene glycol alginate, hydroxypropyl guar, acrylates/$C_{10}$-$C_{30}$ alkyl acrylate crosspolymer, bentonite, laponite, hectorite, magnesium aluminum silicate, amylopectin, cellulose gum, carbomer, chitosan, modified chitosan, glyceryl methacrylate, polyquaterniums, PEG-150 pentaerythrityl tetrastearate, and combinations thereof.

42. The liquid color changing cleansing product as set forth in claim 28 wherein the first nonionic surfactant and second nonionic surfactant are selected from the group consisting of mono and di alkanolamides, amine oxides, alkyl polyglucosides, ethoxylated alcohols, ethoxylated carboxylic acids, ethoxylated amines, ethoxylated amides, ethoxylated alkylolamides, ethoxylated alkylphenols, ethoxylated glyceryl esters, ethoxylated sorbitan esters, and ethoxylated phosphate esters, glycol stearate, glyceryl stearate, and combinations thereof.

43. A liquid color changing cleansing product in a single container comprising a first transparent liquid composition comprising from about 30% (by weight) to about 50% (by weight) of a first water soluble polysaccharide sugar, from about 5% (by weight) to about 30% (by weight) of a first surfactant, from about 1% (by weight) to about 10% (by weight) of a first water soluble salt, and the balance being water and a second colored liquid composition comprising from about 30% (by weight) to about 50% (by weight) of a second water soluble polysaccharide sugar, from about 5% (by weight) to about 30% (by weight) of a second surfactant, from about 1% (by weight) to about 10% (by weight) of a second water soluble salt, from about 0.001% (by weight) to about 10% (by weight) of a coloring agent, and the balance being water.

44. The liquid color changing cleansing product as set forth in claim 43 wherein the first transparent liquid composition and the second colored liquid composition each have a viscosity from about 10,000 cps to about 300,000 cps.

45. The liquid color changing cleansing product as set forth in claim 43 wherein the first transparent liquid composition and the second colored liquid composition each have a viscosity from about 25,000 cps to about 200,000 cps.

46. The liquid color changing cleansing product as set forth in claim 43 wherein the first transparent liquid composition and the second colored liquid composition each have a viscosity from about 50,000 cps to about 100,000 cps.

47. The liquid color changing cleansing product as set forth in claim 43 wherein the first water soluble polysaccharide sugar and second water soluble polysaccharide are selected from the group consisting of fructose, sucrose, and glucose.

48. The liquid color changing cleansing product as set forth in claim 43 wherein the first surfactant and second surfactant are selected from the group consisting of anionic surfactants and nonionic surfactants.

49. The liquid color changing cleansing product as set forth in claim 48 wherein the anionic surfactants are selected from the group consisting of alkyl sulfates, alkyl ether sulfates, alkali metal or ammonia salts or alkyl sulfates, alkali metal or ammonia salts of alkyl ether sulfates, alkyl phosphates, alkyl glyceryl sulfonates, alkyl sulfosuccinates, alkyl taurates, acyl taurates, alkyl sarcosinates, acyl sarcosinates, sulfoacetates, alkyl phosphate esters, mono alkyl succinates, monoalkyl maleates, sulphoacetates, acyl isethionates, alkyl carboxylates, phosphate esters, and combinations thereof.

50. The liquid color changing cleansing product as set forth in claim 48 wherein the nonionic surfactants are selected from the group consisting of mono and di alkanolamides, amine oxides, alkyl polyglucosides, ethoxylated alcohols, ethoxylated carboxylic acids, ethoxylated amines, ethoxylated amides, ethoxylated alkylolamides, ethoxylated alkylphenols, ethoxylated glyceryl esters, ethoxylated sorbitan esters, and ethoxylated phosphate esters.

51. The liquid color changing cleansing product as set forth in claim 43 wherein the first water soluble salt and second water soluble salt are selected from the group consisting of sodium chloride, potassium chloride, ammonium chloride, sodium citrate, potassium citrate, sodium carbonate, potassium carbonate, and ammonium carbonate.

52. The liquid color changing cleansing product as set forth in claim 43 wherein the coloring agent is a dye.

53. The liquid color changing cleansing product as set forth in claim 52 wherein the dye is selected from the group consisting of Blue 1, Blue 4, Brown 1, External Violet 2, External Violet 7, Green 3, Green 5, Green 8, Orange 4, Orange 5, Orange 10, Orange 11, Red 4, Red 6, Red 7, Red 17, Red 21, Red 22, Red 27, Red 28, Red 30, Red 31, Red 33, Red 34, Red 36, Red 40, Violet 2, Yellow 5, Yellow 6, Yellow 7, Yellow 8, Yellow 10, Yellow 11, Acid Red 195, Anthocyanins, Beetroot Red, Bromocresol Green, Bromothymol Blue, Capsanthin/Capsorubin, Curcumin, and Lactoflavin.

54. The liquid color changing cleansing product as set forth in claim 43 wherein the coloring agent is a color additive.

55. The liquid color changing cleansing product as set forth in claim 54 wherein the color additive is selected from the group consisting of aluminum powder, annatto, bismuth citrate, bismuth oxychloride, bronze powder, caramel, carmine, beta carotene, chloraphyllin-copper complex, chromium hydroxide green, chromium oxide greens, copper powder, disodium EDTA-copper, ferric ammonium ferrocyanide, ferric ferrocyanide, guauazulene, guanine, henna, iron oxides, lead acetate, maganese violet, mica, pyrophylite, silver, titanium dioxide, ultramarines, and zinc oxide.

56. The liquid color changing cleansing product as set forth in claim 43 wherein the coloring agent is a pigment or lake.

57. The liquid color changing cleansing product as set forth in claim 56 wherein the pigment or lake is selected from the group consisting of Blue 1 Lake, External Yellow 7 Lake, Green 3 Lake, Orange 4 Lake, Orange 5 Lake, Orange 10 Lake, Red 4 Lake, Red 6 Lake, Red 7 Lake, Red 21 Lake, Red 22 Lake, Red 27 Lake, Red 28 Lake, Red 30 Lake, Red 31 Lake, Red 33 Lake, Red 36 Lake, Red 40 Lake, Yellow 5 Lake, Yellow 6 Lake, Yellow 7 Lake, and Yellow 10 Lake.

\* \* \* \* \*